United States Patent
Shoji et al.

(10) Patent No.: US 8,257,569 B2
(45) Date of Patent: Sep. 4, 2012

(54) CAPILLARY ARRAY UNIT AND CAPILLARY ELECTROPHORESIS APPARATUS

(75) Inventors: Tomohiro Shoji, Hitachinaka (JP); Toshiyuki Sakurai, Honjo (JP); Takashi Gomi, Hitachinaka (JP); Ryoji Inaba, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 325 days.

(21) Appl. No.: 12/352,238

(22) Filed: Jan. 12, 2009

(65) Prior Publication Data

US 2009/0183990 A1    Jul. 23, 2009

(30) Foreign Application Priority Data

Jan. 22, 2008  (JP) .................. 2008-011382

(51) Int. Cl.
*G01N 27/453* (2006.01)
(52) U.S. Cl. ...................... 204/603; 204/601
(58) Field of Classification Search ............. 204/603, 204/604, 605, 450, 451, 452, 453
See application file for complete search history.

(56) References Cited

U.S. PATENT DOCUMENTS

| | | | |
|---|---|---|---|
| 2002/0023839 A1* | 2/2002 | Inaba et al. | 204/451 |
| 2003/0201180 A1* | 10/2003 | Furukawa et al. | 204/452 |
| 2004/0000481 A1* | 1/2004 | Goudberg et al. | 204/461 |
| 2007/0163882 A1* | 7/2007 | Yamazaki et al. | 204/451 |

FOREIGN PATENT DOCUMENTS

| | | |
|---|---|---|
| JP | 2001-281221 | 10/2001 |
| JP | 2001-324473 | 11/2001 |
| JP | 2001-324475 | 11/2001 |
| JP | 2005-077293 | 3/2005 |

* cited by examiner

*Primary Examiner* — Jeffrey T Barton
*Assistant Examiner* — J. Christopher Ball
(74) *Attorney, Agent, or Firm* — McDermott Will & Emery LLP

(57) ABSTRACT

In a capillary electrophoresis apparatus, a capillary array unit has a capillary array including capillaries having a capillary head and a detection unit, a frame for supporting the capillary array, and a load header for holding cathode ends of the capillaries. The frame has separators for separating and holding the capillaries. The capillary head, the detection unit, and the separators are disposed along one linear line. With this arrangement, there is provided the capillary array unit and the capillary electrophoresis apparatus which are arranged such that a job for mounting the capillary array can be executed easily.

12 Claims, 4 Drawing Sheets

CAPILLARY ARRAY UNIT AND CAPILLARY ELECTROPHORESIS APPARATUS

BACKGROUND OF THE INVENTION

1. Field of the Invention

The invention relates to a capillary array unit and a capillary electrophoresis apparatus using the capillary array unit.

2. Description of the Related Art

A capillary electrophoretic method has become widespread as a technology for separating and analyzing a lot of living body specimens such as deoxyribonucleic acid (DNA). One of technical advantages of the method resides in excellent heat radiation characteristics obtained from the surface-to-volume ratio of a capillary. The heat radiation characteristics realize high speed separation of specimens with high resolution by electrophoresis using a high voltage.

Japanese Patent Application Laid-Open (JP-A) Publication No. 2001-281221 discloses a pump mechanism for filling a capillary with polymer as a separation medium. Further, the publication discloses a method of making use of motor stalling torque as a means for generating pressure for filling the polymer.

JP-A Publication No. 2001-324473 discloses an electrophoresis apparatus provided with an oven that can accommodate capillaries having different lengths or a different number of capillaries according to a type of analysis and a throughput needed by a user. Further, the oven uses a peltier element as a heat source and can set a temperature from a room temperature or less up to 50° C. or more.

JP-A Publication No. 2001-324475 discloses a capillary array which can be replaced by a user. The capillary array has such a structure that it is held at three positions of a specimen introduction side end, an optical detection unit, and a polymer solution supply end portion. The polymer solution supply end portion of the capillary array is connected to a pump mechanism of an electrophoresis apparatus.

In a capillary electrophoresis apparatus, when a specimen and a type of an application change, a capillary array is replaced according to it. The capillary array is replaced by a user. The capillary has a relatively rigid type and a relatively flexible type. In the case of flexible type, a capillary replacement job can be relatively simply executed.

However, in the case of rigid type, the capillary replacement job is difficult. The capillary is formed in a linear shape, or in a curved shape in which the capillary is warped due to a weight of a component. When the capillary is mounted at a predetermined position of an oven and the like, it must be deformed. Since a capillary deforming job is difficult, the capillary replacement job becomes difficult.

Further, when a lot of capillaries are employed, since a capillary array becomes rigid, a mounting job becomes difficult.

Accordingly, an object of the invention is to provide a capillary electrophoresis apparatus arranged such that a capillary array mounting job can be executed easily.

SUMMARY OF THE INVENTION

The invention relates to a capillary array unit and a capillary electrophoresis apparatus using the capillary array unit. The capillary array unit has a capillary array including capillaries having a capillary head and a detection unit, a frame for supporting the capillary array, and a load header for holding cathode ends of the capillaries. The frame has at least one separator for separating as well as holding the capillaries. The capillary array is held in a predetermined shape by the capillaries passing through the separator.

According to the invention, capillary array mounting job can be executed easily.

Figure 1:
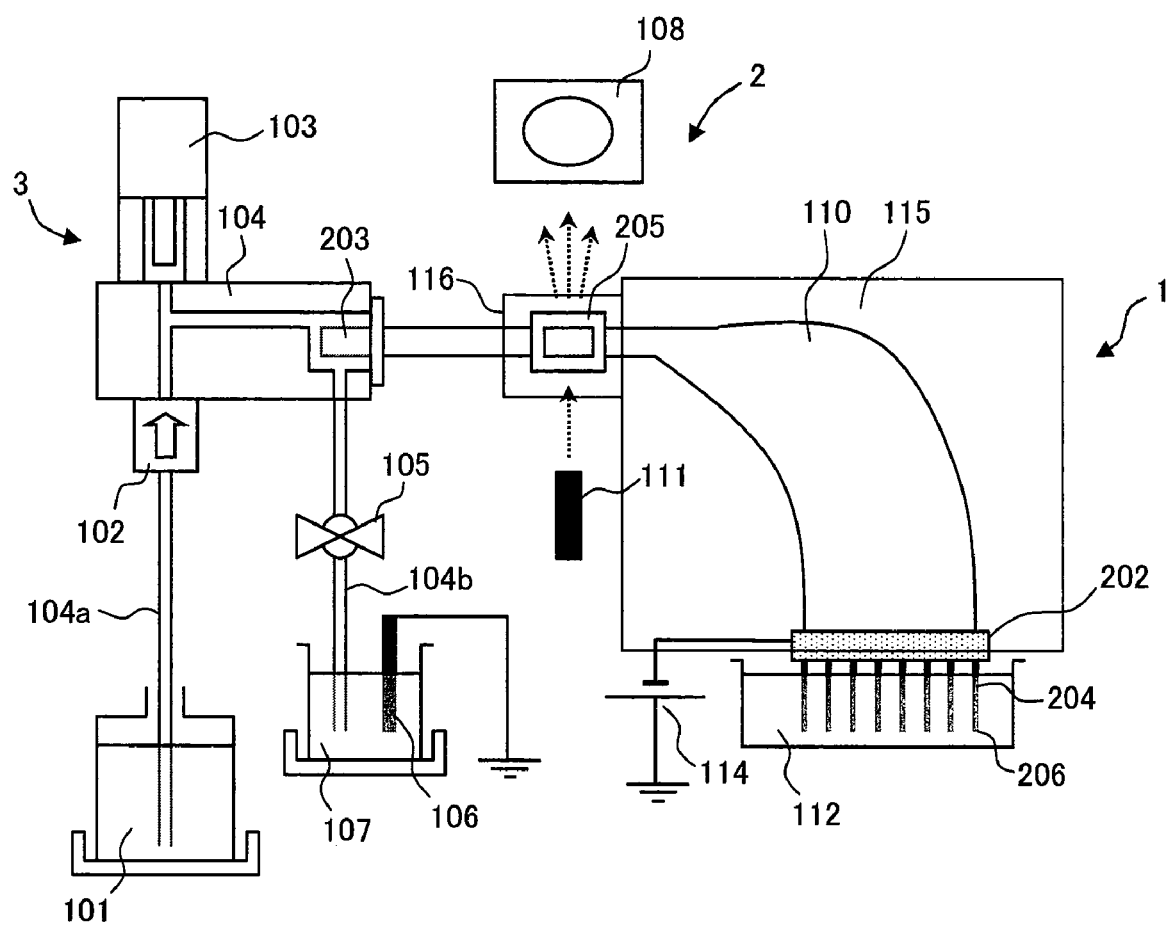
FIG. 1 is a view showing a basic arrangement of a capillary electrophoresis apparatus according to the invention.

DESCRIPTION OF REFERENCE NUMERALS 101 polymer bottle
102 check valve
103 pump
104 block
105 buffer valve
106 anode electrode
107 buffer reservoir
108 optical detection device
110 capillary array
111 light source
112 buffer vessel
113 electrode
114 high voltage power supply
115 oven
116 detection unit holder
201 capillaries
202 load header
202a grip
203 capillary head
204 cathode electrode
205 detection unit
205a, 205b opening
300 frame
301 first leg
302 first support portion
303 second leg
304 second support portion
305, 306 second bridges
307 connecting portion
311, 312, 313 shafts
321, 322, 323 separators

DESCRIPTION OF THE PREFERRED EMBODIMENTS

FIG. 1 is a schematic view showing a basic arrangement of a capillary electrophoresis apparatus. The capillary electrophoresis apparatus has a capillary electrophoresis unit 1 including one or a plurality of capillaries, an optical detection unit 2 for optically detecting specimens separated by an electrophoresis medium in the capillary, and a polymer injection mechanism 3 for injecting high viscosity polymer solution (hereinafter, called polymer) as the electrophoresis medium into the capillary.

The capillary electrophoresis unit 1 has a capillary array 110, an oven (constant temperature oven) 115, a buffer reservoir (buffer vessel) 112, and a high voltage power supply 114.

The capillary array 110 includes one or a plurality of capillaries, but here it is assumed that it includes 16 capillaries or 24 capillaries. The capillaries are quartz pipes and the outside surfaces thereof are coated with polyimide resin. The capillaries include a type having strong rigidity with a relatively large diameter and a type having flexibility with a relatively small diameter. As an example of the type having the strong rigidity, there is a capillary having an outside diameter of 320 µm and an inside diameter of 50 µm. The polyimide coating has a thickness of 20 µm. Accordingly, the polyimide coating has an outside diameter of 360 µm. As an example of the type having flexibility, there is a capillary having an outside diameter of 125 µm and an inside diameter of 50 µm. The thickness of the polyimide coating is 12.5 µm. Accordingly, the outside diameter of the polyimide coating is 150 µm.

According to the example, it is assumed that the capillary array 110 includes the capillaries of the type having the strong rigidity with the relatively large diameter. The outside diameter of the capillaries is 0.3 to 0.7 mm and the inside diameter thereof is about 0.02 to 0.2 mm.

An end of the capillary array 110 is arranged as a capillary head 203 in which bundled capillaries are bonded. The other end of the capillary array 110 is held by a load header 202. The load header 202 is fixed to the oven 115.

The load header 202 is provided with pipe-like cathode electrodes 204. The capillaries pass through the cathode electrodes 204 and project from lower ends of the cathode electrodes. With this arrangement, capillary cathode ends 206 are dipped in a buffer solution in the buffer reservoir 112.

The oven 115 accommodates the capillary array 110 and adjusts the temperature of the capillary array 110. A peltier element is used as a heat source of the oven 115 and a temperature from a lower temperature than a room temperature to a high temperature of 50° C. or more can be set.

The polymer injection mechanism 3 has a pump 103 including a plunger, a block 104 including a flow path therein, a polymer bottle 101 storing polymer, and a buffer vessel 107 storing the buffer solution. An anode electrode 106 is dipped in the buffer solution of the buffer vessel 107. The inside diameter of the flow path in the block 104 is 0.5 to 2 mm, which is several times to several tens of times larger than the inside diameter of the capillaries. This is for avoiding occurrence of a voltage loss in electrophoresis.

The pump 103, the capillary head 203, and two pipes 104a, 104b are connected to the block 104. The pump 103, the capillary head 203, and the two pipes 104a, 104b are connected to each other by the flow path in the block 104. The first pipe 104a connects the block 104 and the polymer in the polymer bottle 101. The first pipe 104a is provided with a check valve 102. The second pipe 104b connects the block 104 and the buffer solution in the buffer reservoir 107. The second pipe 104b is provided with an electrically driven buffer valve 105.

An amount of the polymer, which is sufficient for a continuous operation, is stored in the polymer bottle 101. An exhaust valve is provided with to the polymer bottle 101 so that the inside of the polymer bottle 101 has not a negative pressure even when the polymer is sucked therefrom, and further a sufficient gap is formed at a tube insertion port. The polymer bottle 101 is disposed at a position lower than the buffer vessel 107. This is for preventing the polymer from flowing backward from the polymer bottle 101 into the buffer vessel 107 by a pressure due to a difference of height. On the contrary, backflow of the polymer or the buffer liquid to the polymer bottle 101 is prevented by the check valve 102. The liquid surfaces of the buffer liquids in the two buffer reservoirs 112, 107 are kept in the same height.

When the polymer is injected into the capillaries of the capillary array 110, the electrically driven buffer valve 105 is closed. With this operation, a flow path between the capillary array 110 and the buffer reservoir 107 is closed. The polymer in the polymer bottle 101 is injected into the capillaries by driving the pump 103. When electrophoresis is executed, the buffer valve 105 is opened, and the flow path between the capillary array 110 and the buffer reservoir 107 is connected.

The optical detection unit 2 has a light source 111 and an optical detection device 108. The optical detection unit 2 is disposed at a detection unit 205 provided with to the capillary array 110. The detection unit 205 is mounted on a detection unit holder 116. The light source 111 generates laser light as exciting light. The coating of the capillaries is removed in the detection unit 205, and the quartz pipes are exposed. The exciting light from the light source 111 radiates subjects to be detected which are subjected to the electrophoresis in the capillaries in the detection unit 205. Fluorescence is generated from the subjects to be detected. The fluorescence is detected by the optical detection device 108.

An electrophoresis method will be explained. Although omitted in FIG. 1, the electrophoresis apparatus has an auto sampler for transporting a sample tray and the buffer vessel 112. The sample tray is disposed at the cathode ends 206 of the capillaries by the auto sampler. First, the sample tray is disposed below the cathode ends 206 of the capillaries and then raised. The sample tray has a lot of wells which accommodate samples including subjects to be inspected such as fluorescently-labeled DNAs and the like. The cathode ends 206 of capillaries 201 are dipped into the samples in the wells of the sample tray. Next, a high voltage of about several kV from the high voltage power supply 114 is applied to between the anode electrode 106 and the cathode electrodes 204. The subjects to be inspected such as fluorescently-labeled DNAs are introduced into the capillaries through the cathode ends 206 of capillaries. Thereafter, as shown in FIG. 1, the cathode ends 206 of the capillaries are dipped into the buffer vessel 112. The subjects to be detected are separated while they move in the capillaries. When the subjects to be detected that are fluorescently-labeled pass through the detection unit 205, exciting light is radiated thereto from the light source 111. The subjects to be detected generate fluorescence by the exciting light. The fluorescence is detected by the optical detection device 108.

An operation of the polymer injection mechanism will be explained. The pump 103 will be explained assuming that a direction in which a plunger is forcibly inserted into a chamber is a forward rotation direction of a motor, and a direction in which the plunger is pulled in is a backward rotation direction of the motor. First, the valve 105 is closed. Next, the motor is rotated backward. The plunger is pulled in, and the polymer in the polymer bottle 101 is sucked into the chamber of the pump 103 through the flow path in the block 104. Next, the motor is rotated forward. The plunger is forcibly inserted, and the polymer in the chamber of the pump 103 is forcibly charged into the flow path in the block 104. At the time, the polymer in the chamber of the pump 103 is prevented from flowing backward to the polymer bottle 101 by the action of the check valve 102. Accordingly, the polymer flows into the capillaries through the flow path in the block 104 and flows out from the cathode ends 206 of the capillaries. Finally, the valve 105 is opened to prepare for the electrophoresis.

Figure 2A:
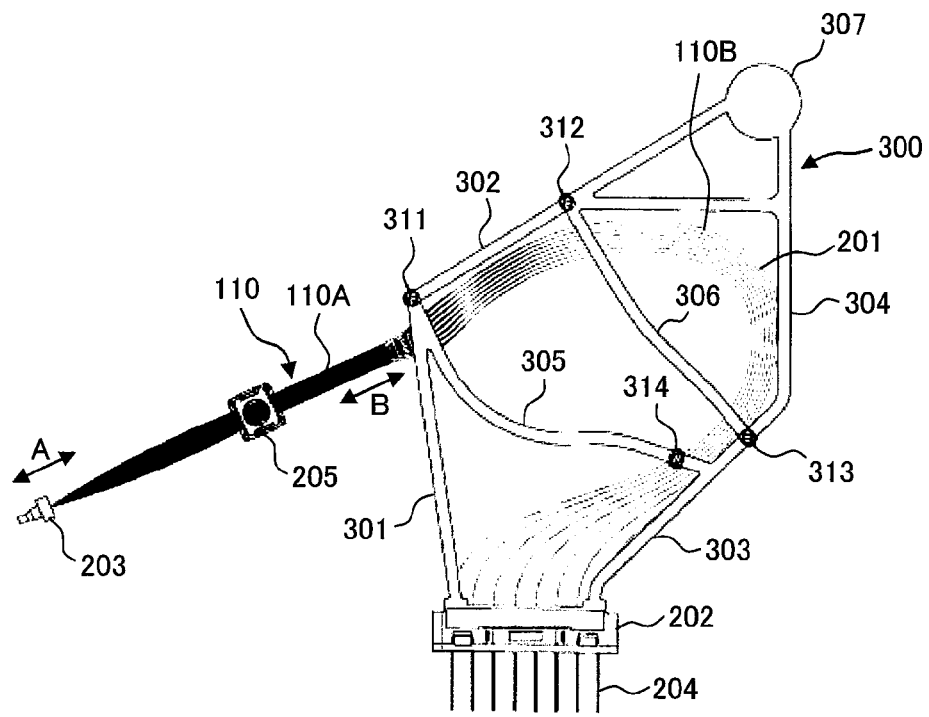
FIG. 2A and FIG. 2B are views showing a basic arrangement of a capillary array according to the invention.
Figure 2B:
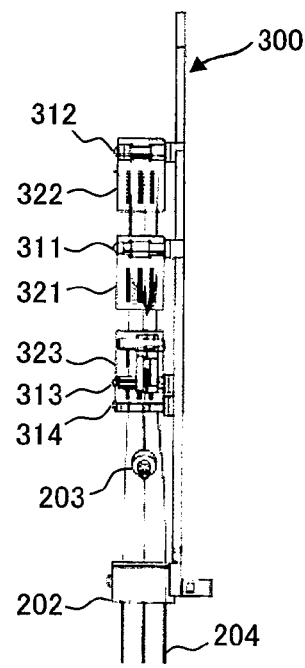

An example of the capillary array unit of the invention will be explained referring to FIG. 2A and FIG. 2B. FIG. 2A shows a front arrangement of the capillary array unit of the example, and FIG. 2B shows a side arrangement thereof. The capillary array unit of the example has the capillary array 110 and a frame 300 for holding it. As shown in FIG. 2A, the frame 300 has a first leg 301, a first support portion 302, a second leg 303, a second support portion 304, and first and second bridges 305, 306. The frame 300 is arranged such that it holds the capillary array 110 in one flat plane. The two legs 301, 303 are fixed to the load header 202. The two support portions 302, 304 are connected by a connecting portion 307. The first bridge 305 bridges a connecting point of the first leg 301 and the first support portion 302 and the second leg 303. The second bridge 306 bridges the first support portion 302 and the second leg 303.

Two shafts 311, 312 are provided with to the first support portion 302. A shaft 313 is provided with to the second leg 303.

As shown in FIG. 2B, these shafts 311, 312, and 313 extend so as to be orthogonal to a plane constituting the frame 300. Separators 321, 322, and 323 are mounted on these shafts 311, 312, and 313. The separators are formed like a film or sheet and have as many holes as the number of the capillaries formed therethrough. Each hole has an inside diameter slightly larger than the outside diameter of the capillaries, which is set to, for example, about 1 mmφ. One capillary passes through each hole. With this arrangement, all the capillaries pass through the holes of the separators so as to be held thereby.

The separators separate the capillaries from each other so that the capillaries are prevented from being tangled with each other and from being made into a bundle state by being gathered closely. The number of the separators may be increased or decreased according to the length of the capillaries. Ordinarily, longer capillaries increase the number of separators.

The capillary array 110 has a plurality of the capillaries 201. The capillary array 110 of the example has 24 capillaries 201. According to the example, it is assumed that the capillary array 110 includes the capillaries of the type having the relatively large diameter and the strong rigidity. The outside diameter of the capillaries is 0.3 to 0.7 mm and the inside diameter thereof is about 0.02 to 0.2 mm.

One end of the capillary array 110 is arranged as the capillary head 203 in which bundled capillaries are bonded. The other end of the capillary array 110, that is, the cathode ends are held by a pipe-like electrode provided with to the load header 202.

Since the capillaries of the example have a relatively large amount of rigidity, they have a linear shape as long as no external force and no restriction force are applied thereto. In the example, the capillary array is restricted by the load header 202 and the frame 300. As shown in the drawing, the capillary array has a linear portion 110A and a curved portion 110B. The linear portion 110A projects from the frame 300 and is not restricted by the frame 300. The linear portion 110A includes the capillary head 203 and the detection unit 205. The linear portion 110A keeps an approximately linear state regardless of the weights of the capillary head 203 and the detection unit 205.

The curved portion 110B is restricted by the load header 202 and the separators. When no external force is applied to the capillary array, the shape of the capillary array is determined by the positions of the load header 202 and the separators.

Next, the shape of the capillary array will be explained. According to the example, the linear portion 110A of the capillary array is disposed along the first support portion 302 of the frame. The separators 321 mounted on the capillary head 203, the detection unit 205, and the shafts 311 are disposed on a linear line. According to the capillary array unit of the example, approximately one half portion of the capillary array is disposed in an approximately linear shape.

An external force is applied to the capillary head 203 in the direction of an arrow A. Thus, the linear portion 110A moves along the direction shown by the arrow A. With this operation, the capillaries slide through holes in the separators 321, 322. As a result, the capillary head 203 moves in the direction of an arrow A.

FIG. 2A shows the shape of the capillary array of the example when no external force is applied to the capillary array. When the capillary array unit of the example is mounted on the electrophoresis apparatus, the capillary array is held in a shape shown in FIG. 2A. That is, even if the capillary array unit of the example is mounted on the electrophoresis apparatus, the capillary array is kept in the shape shown in FIG. 2A.

Accordingly, the relative positional relation between the capillary head 203, the detection unit 20, and the load header 202 in the capillary array shown in FIG. 2A is equal to the relative positional relation between the mounting positions of the capillary head 203, the detection unit 205, and the load header 202 in the capillary array mounted on the electrophoresis apparatus.

According to the example, the positions of the separators are selected so that the capillary array has the shape shown in FIG. 2A. As described above, when the positions of the separators are selected, it is not necessary to apply an external force to the capillary array 110 in order to mount the capillary array 110 on the electrophoresis apparatus. Accordingly, the capillary array can be mounted without being deformed.

According to the example, as shown in FIG. 2A, the capillary head is disposed below and the linear portion 110A of the capillary array is disposed in inclination. This will be explained. In the capillary electrophoresis apparatus shown in FIG. 1, it is preferable to make the pipe 104b connected to the block 104 short to reduce an usage amount of the polymer. When the pipe 104b is made short, not only the usage amount of the polymer can be reduced but also a material cost of the pipe 104b can be reduced. When the pipe 104b is made short, it is necessary to lower the block 104 or to raise the buffer reservoir 107. On the other hand, it is necessary to make the liquid surface of the buffer reservoir 107 and the liquid surface of the buffer reservoir 112 uniform. Therefore, the buffer reservoir 107 cannot be raised. Thus, the block 104 is lowered. That is, the block 104 is disposed at a position as low as possible. When the block 104 is lowered, the mounting position of the capillary head is also lowered. Accordingly, as shown in FIG. 2A, one half portion of the capillary array is inclined.

Figure 3:
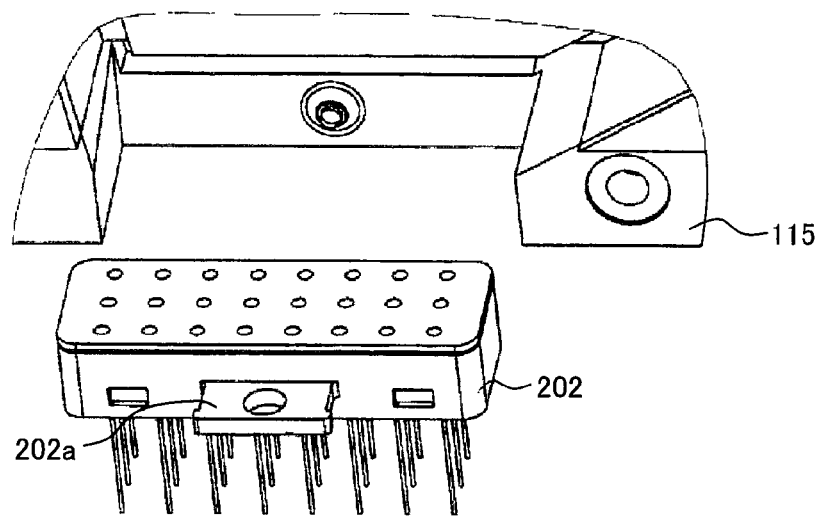
FIG. 3 is a view showing a mounting portion of a load header of the capillary electrophoresis apparatus according to the invention.

Next, a sequence for mounting the capillary array according to the invention will be explained referring to FIGS. 3, 4, 5, and 6. First, the load header 202 is mounted on the oven 115. This will be explained referring to FIG. 3. FIG. 3 shows both a part of a lower end of the oven 115 and the load header 202. The capillary array mounted on the load header is not shown. A grip 202a is provided with to the load header 202. A user grips the grip 202a and inserts the load header 202 into a recessed portion of the oven 115. The load header 202 has grooves on both the sides thereof, and a projection is provided inside the recessed portion of the oven 115. When the load header 202 is inserted into the recessed portion of the oven 115, the groove of the load header 202 is engaged with the recessed portion of the oven 115.

Figure 4:
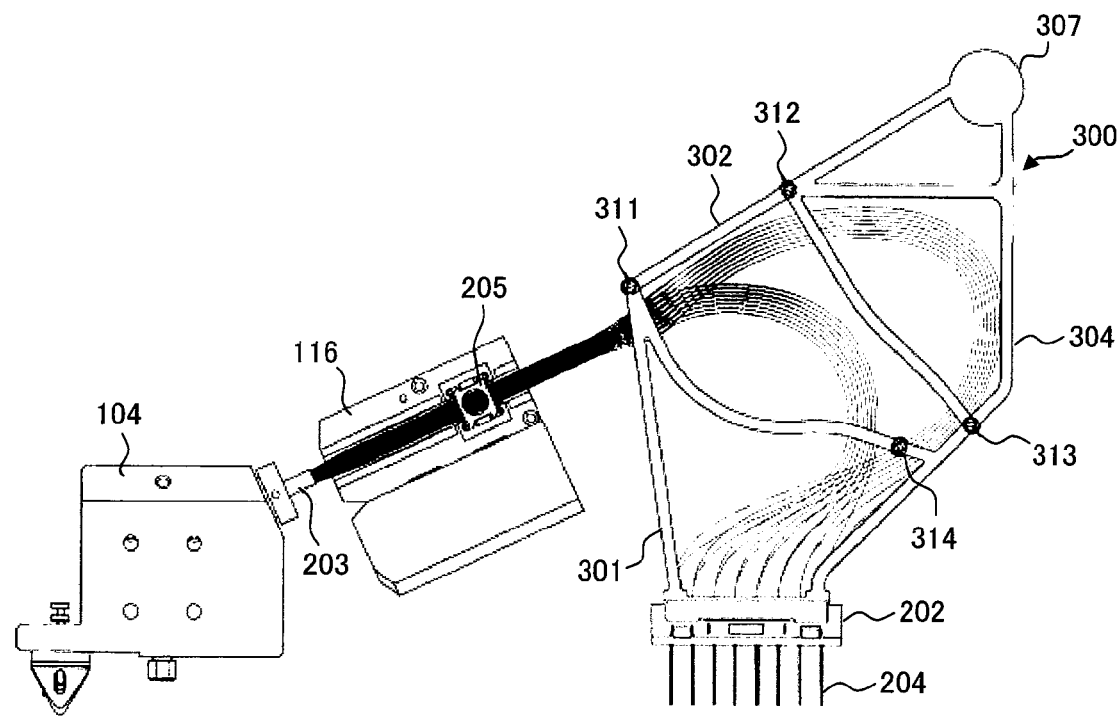
FIG. 4 is a view showing a capillary array after the load header of the capillary electrophoresis apparatus according to the invention is mounted.
Figure 5:
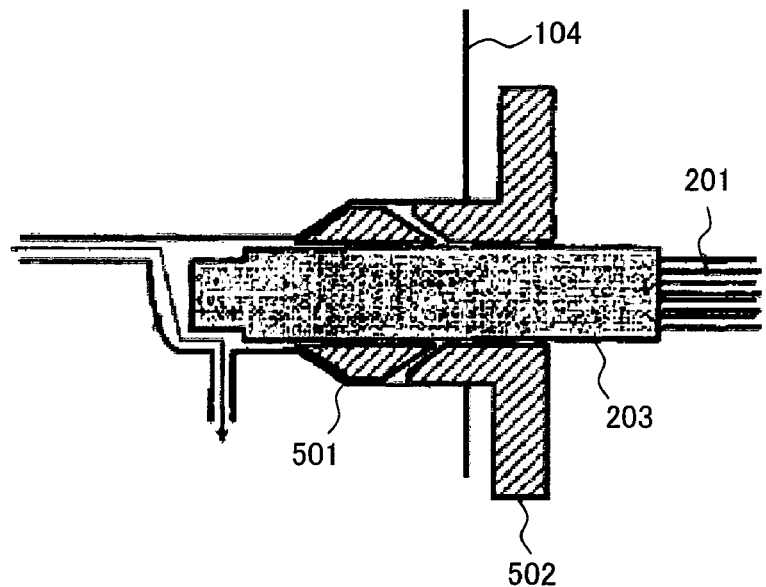
FIG. 5 is a view showing a mounting portion of a capillary head of the capillary electrophoresis apparatus according to the invention.
Figure 6:
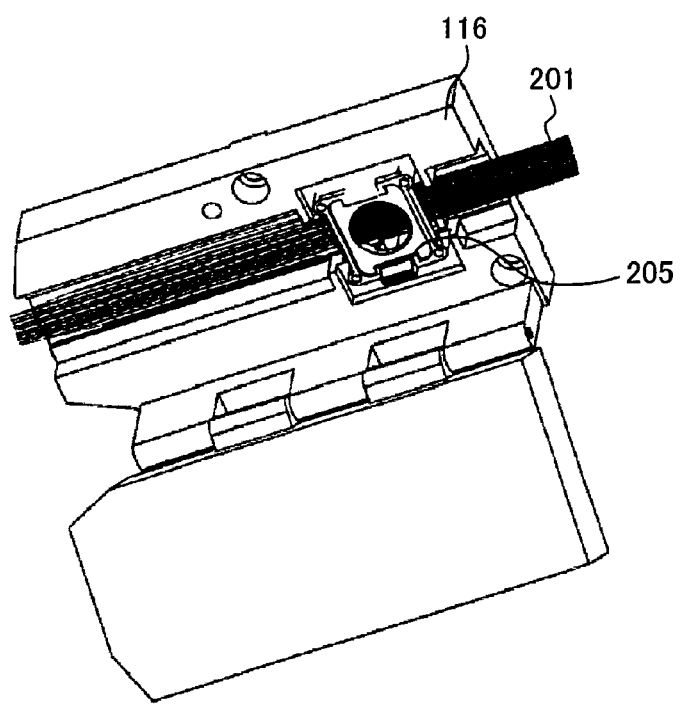
FIG. 6 is a view showing a mounting portion of a detection unit of the capillary electrophoresis apparatus according to the invention.

FIG. 4 shows a state that the load header 202 is mounted on the oven 115. The shape of the capillary array 110 shown in FIG. 2A is kept as it is. In the example, the capillary head 203 is disposed in the vicinity of the mounting portion of the block 104 of the polymer injection mechanism 3. Further, the detection unit 205 is disposed in the vicinity of the mounting portion of the detection unit holder 116.

Next, the capillary head 203 is mounted on the block 104 of the polymer injection mechanism 3. This will be explained referring to FIG. 5. A ferrule 501 is charged in a hole of the block 104 and the capillary head 203 is caused to pass through the ferrule 501. Otherwise, the capillary head 203 may be caused to pass through the ferrule 501 and then the capillary head 203 may be inserted into a hole of the block 104 together with the ferrule 501. At the time, the capillary head 203 can be moved in a forward and backward direction by a small amount of force as explained referring to FIG. 2A and FIG. 2B. Next, a set screw 502 is screwed so that the ferrule 501 is pressed and smashed. With this operation, space between the capillary head 203 and the block 104 is sealed, and the capillary head 203 is fixed to the block 104.

As shown in FIG. 4, the capillary head 203 is disposed in the vicinity of the mounting portion of the block 104 of the polymer injection mechanism 3. Accordingly, since the job is only to slightly move the capillary head 203 in the forward and backward direction, it can be easily executed.

Finally, the detection unit 205 is mounted on the detection unit holder 116. This will be explained referring to FIG. 6. The detection unit 205 is fit into a frame equipped with to the detection unit holder 116. Next, a lid is closed.

As shown in FIG. 4, the detection unit 205 is disposed in the vicinity of the mounting portion of the detection unit holder 116. Accordingly, since the job is only to slightly move the detection unit 205 in a lateral direction, it can be executed easily.

As described above, according to the example, when a job for mounting the capillary array on the electrophoresis apparatus is carried out, it is not necessary to deform the capillary array. Accordingly, a job for replacing the capillary array can be easily executed.

The example of the invention has been explained above, but persons skilled in the art can easily understand that the invention is not limited to the example and can be variously changed within the scope of the invention according to the claims.

What is claimed is:

1. A capillary array unit comprising:
   a capillary array including one or more capillaries capable of being filled with an electrophoresis medium therein; a frame for holding the capillary array; and a load header for supporting cathode ends of the capillaries, wherein:
   the frame comprises a plurality of separators for separating and holding the capillaries in a predetermined shape by the capillaries passing through the separators,
   the capillary array comprises a linear portion projecting from the frame and a remaining portion held by the separators provided on the frame, the linear portion having a capillary head at an extreme end and a detection unit adjacent to the capillary head, the remaining portion having the cathode end opposite to the capillary head,
   the remaining portion of the capillary array includes a first portion which is held in a substantially linear shape by at least a first separator and a second separator adjacent to the detection unit, and a second portion which is held in a curved shape by at least a third separator spaced from the first and second separators,
   the capillary head, the detection unit, the first separator and the second separator are disposed along one linear line, and,
   the separators are disposed on the frame so that when the capillary head is moved in a direction along the linear portion, the linear portion and the first portion of the remaining portion which is held in a substantially linear shape move freely in a direction along the linear portion.

2. The capillary array unit according to claim 1, wherein the relative position between the capillary head and the detection unit after the capillary array unit is mounted on the electrophoresis apparatus is set the same as the relative position between the capillary head and the detection unit before the capillary array unit is mounted on the electrophoresis apparatus.

3. The capillary array unit according to claim 2, wherein the shape of the capillary array after the capillary array unit is mounted on the electrophoresis apparatus is made the same as the shape before the capillary array unit is mounted on the electrophoresis apparatus.

4. The capillary array unit according to claim 1, wherein the frame comprises first and second legs fixed to the load header, first and second support portions connected to the first and second legs, respectively, a connecting portion for connecting the first and second support portions, a first bridge for bridging between the first and second legs, and a second bridge for bridging between the first and second support portions and is arranged to hold the capillary array on one flat plane.

5. A capillary electrophoresis apparatus comprising a capillary array unit comprising a capillary array including one or more capillaries capable of being filled with an electrophoresis medium therein, a frame for supporting the capillary array, and a load header for supporting cathode ends of the capillaries, an oven for holding the capillary array at a predetermined temperature, an injection mechanism for injecting an electrophoresis medium into the capillaries, and an optical detection unit having a light source for radiating exciting light and a light receiving portion for detecting fluorescence, wherein:
   the frame comprises a plurality of separators for separating and holding the capillaries in a predetermined shape by the capillaries passing through the separators,
   the capillary array comprises a linear portion projecting from the frame and a remaining portion held by the separators provided on the frame, the linear portion having a capillary head at an extreme end and a detection unit adjacent to the capillary head, the remaining portion having the cathode end at an end opposite to the capillary head, and the capillary head being connected to the injection mechanism,
   the remaining portion of the capillary array includes a first portion which is held in a substantially linear shape by at least a first and a second separator adjacent to the detection unit, and a second portion which is held in a curved shape by at least a third separator spaced from the first and second separators,
   the capillary head, the detection unit, and the at least the first separator and the second separators are disposed along one linear line, and
   the separators are disposed on the frame so that when the capillary head is moved in a direction along the linear portion, the linear portion and the first portion of the remaining portion which is held in a substantially linear shape move freely in a direction along the linear portion.

6. The capillary electrophoresis apparatus according to claim 5, wherein the relative position between the capillary head and the detection unit after the capillary array unit is mounted on the electrophoresis apparatus is set the same as the relative position between the capillary head and the detection unit before the capillary array unit is mounted on the electrophoresis apparatus.

7. The capillary electrophoresis apparatus according to claim 6, wherein the shape of the capillary array after the capillary array unit is mounted on the electrophoresis apparatus is made the same as the shape before the capillary array unit is mounted on the electrophoresis apparatus.

8. The capillary electrophoresis apparatus according to claim 5, wherein the frame comprises first and second legs fixed to the load header, first and second support portions connected to the first and second legs, respectively, a connecting portion for connecting the first and second support portions, a first bridge for bridging between the first and second legs, and a second bridge for bridging between the first and second support portions and is arranged to hold the capillary array on one flat plane.

9. A capillary electrophoresis apparatus comprises a capillary array unit comprising a capillary array including one or more capillaries capable of being filled with an electrophoresis medium therein, a frame for supporting the capillary array, and a load header for supporting cathode ends of the capillaries, an oven for holding the capillary array at a predetermined temperature, an injection mechanism for injecting an electrophoresis medium into the capillaries, and an optical detection unit having a light source for radiating exciting light and a light receiving portion for detecting fluorescence, wherein:

the capillary array comprises a linear portion projecting from the frame and a remaining portion held by the frame, the linear portion has the capillary head at an extreme end and a detection unit adjacent to the capillary head, and the remaining portion has the cathode end at an end opposite to the capillary head, and the capillary head is connected to the injection mechanism, the linear portion is disposed in inclination so that the capillary head is located at a position lower than the detection unit, the frame comprises a plurality of separators for separating and holding the capillaries in a predetermined shape by the capillaries passing through the separators, the remaining portion of the capillary array includes a first portion which is held in a substantially linear shape by at least a first separator and a second separator adjacent to the detection unit, and a second portion which is held in a curved shape by at least a third separator spaced from the first and second separators, the capillary head, the detection unit, and the at least first and second separator are disposed along one linear line, and the separators are disposed on the frame so that when the capillary head is moved in a direction along the linear portion, the linear portion and the first portion of the remaining portion which is held in a substantially linear shape move freely in a direction along the linear portion.

10. The capillary electrophoresis apparatus according to claim 9, wherein the relative position between the capillary head and the detection unit after the capillary array unit is mounted on the electrophoresis apparatus is set the same as the relative position between the capillary head and the detection unit before the capillary array unit is mounted on the electrophoresis apparatus.

11. The capillary electrophoresis apparatus according to claim 9, wherein the shape of the capillary array after the capillary array unit is mounted on the electrophoresis apparatus is made the same as the shape before the capillary array unit is mounted on the electrophoresis apparatus.

12. The capillary electrophoresis apparatus according to claim 9, wherein the frame comprises first and second legs fixed to the load header, first and second support portions connected to the first and second legs, respectively, a connecting portion for connecting the first and second support portions, a first bridge for bridging between the first and second legs, and a second bridge for bridging between the first and second support portions and is arranged to hold the capillary array on one flat plane.

* * * * *